United States Patent
Momma (10) Patent No.: US 7,233,693 B2
(45) Date of Patent: Jun. 19, 2007

(54) METHODS AND SYSTEMS FOR COMPUTER ANALYSIS OF SKIN IMAGE

(75) Inventor: Tomoyuki Momma, Tokyo (JP)

(73) Assignee: Inforward, Inc., Tokyo (JP)

( * ) Notice: Subject to any disclaimer, the term of this patent is extended or adjusted under 35 U.S.C. 154(b) by 834 days.

(21) Appl. No.: 10/424,984

(22) Filed: Apr. 29, 2003

(65) Prior Publication Data

US 2004/0218810 A1    Nov. 4, 2004

(51) Int. Cl.
  *G06K 9/00* (2006.01)
(52) U.S. Cl. ..................................... 382/162
(58) Field of Classification Search ............... 382/100, 382/118, 128, 162, 164, 165, 167, 170, 173, 382/276; 356/303, 406; 600/160, 475
  See application file for complete search history.

(56) References Cited

U.S. PATENT DOCUMENTS

| | | | |
|---|---|---|---|
| 4,170,987 A * | 10/1979 | Anselmo et al. ............ 600/475 |
| 6,081,612 A * | 6/2000 | Gutkowicz-Krusin et al. ........................ 382/128 |
| 6,208,749 B1 * | 3/2001 | Gutkowicz-Krusin et al. ........................ 382/128 |
| 6,571,003 B1 * | 5/2003 | Hillebrand et al. ......... 382/118 |
| 6,947,594 B2 * | 9/2005 | Watanabe et al. ........... 382/167 |
| 6,993,167 B1 * | 1/2006 | Skladnev et al. ........... 382/128 |
| 2003/0067545 A1 | 4/2003 | Giron et al. |
| 2003/0149347 A1 | 8/2003 | Kauffmann et al. |

FOREIGN PATENT DOCUMENTS

| | | |
|---|---|---|
| JP | 7-055447 | 3/1995 |
| JP | 7-231883 | 9/1995 |
| JP | 7-289524 | 11/1995 |
| WO | WO 00/76398 A1 | 12/2000 |

* cited by examiner

*Primary Examiner*—Jose L. Couso
(74) *Attorney, Agent, or Firm*—Foley & Lardner LLP (57) ABSTRACT

Methods and systems for digitally evaluating skin conditions based on a skin image. A digital image of a surface of a human face is received from a camera set in an image capturing device. The surface is illuminated with white light and placed apart from the camera when the digital image is acquired by the camera. A plurality of kinds of analysis (e.g., evaluation of a skin color, evaluation of pigmented spots, evaluation of pores, and/or evaluation of wrinkles) is performed on the received digital image to produce a plurality of data representing skin conditions of the human body. The produced data are output to a display or a database.

20 Claims, 10 Drawing Sheets

METHODS AND SYSTEMS FOR COMPUTER ANALYSIS OF SKIN IMAGE

BACKGROUND OF THE INVENTION

1. Field of the Invention

The present invention is generally related to computer analysis of skin images. The invention is more particularly related to methods and systems for processing digital images of human skin to evaluate the conditions of the skin for dermatology. Dermatology includes medical applications and cosmetics applications.

2. Background

Information technology has penetrated into the medical industry. For example, pathologists now enjoy the benefits of CCD cameras, image processing software, and data filing devices, to store and analyze an enormous number of digital images of diseased or damaged organs with pathological changes. These techniques are also used to implement telemedicine in the area of pathology, which is called telepathology.

On the other hand, there have been few trials to implement digital image analysis or telemedicine in the area of dermatology. This is because there has been no established way to digitally evaluate any physical change occurring on the surface of human skin. In other words, there has been no way to measure the conditions of human skin such that the measured indices can represent significant elements for diagnosis and/or treatment of the human skin.

Therefore, the evaluation of the conditions of human skin based on its digitally captured image would realize not only the above-mentioned telemedicine but also so-called "evidence-based medicine" and "informed consent" in the medical examination and treatment. It would also help a clinical education. In addition, such skin evaluation would be used in the cosmetics industry for developing cosmetics products and/or for selling such cosmetics to customers with one-to-one consultation.

SUMMARY OF THE INVENTION

Methods and systems consistent with the invention provide a skin image processing to digitally evaluate the conditions of the skin. First, a digital image of a surface of a portion of a human body is received from a camera. The surface is illuminated with white light and placed apart from the camera when the digital image is acquired by the camera.

Next, a plurality of kinds of analysis is performed on the received digital image to produce a plurality of data representing skin conditions of the human body. The plurality of kinds of analysis may include evaluation of a skin color, evaluation of pigmented spots, evaluation of pores, and/or evaluation of wrinkles. Thereafter, the produced data are output to a display or a database.

Methods and systems consistent with the invention may be implemented in a computer, and the computer may be connected with an image capturing device including the camera. The image capturing device can provide a fixed distance between the camera and the surface of the portion of the human body.

As described hereafter, other aspects of the invention exist. Thus, this summary of the invention is intended to provide a few aspects of the invention and is not intended to limit the scope of the invention described and claimed herein.

BRIEF DESCRIPTION OF THE DRAWINGS

The accompanying drawings are incorporated in and constitute a part of this specification. The drawings exemplify certain aspects of the invention and, together with the description, serve to explain some principles of the invention.

DETAILED DESCRIPTION

The following detailed description refers to the accompanying drawings. Although the description includes exemplary implementations, other implementations are possible and changes may be made to the implementations described without departing from the spirit and scope of the invention. The following detailed description and the accompanying drawings do not limit the invention. Instead, the scope of the invention is defined by the appended claims. Wherever possible, the same reference numbers will be used throughout the drawings and the following description to refer to the same or like parts.

Figure 1:
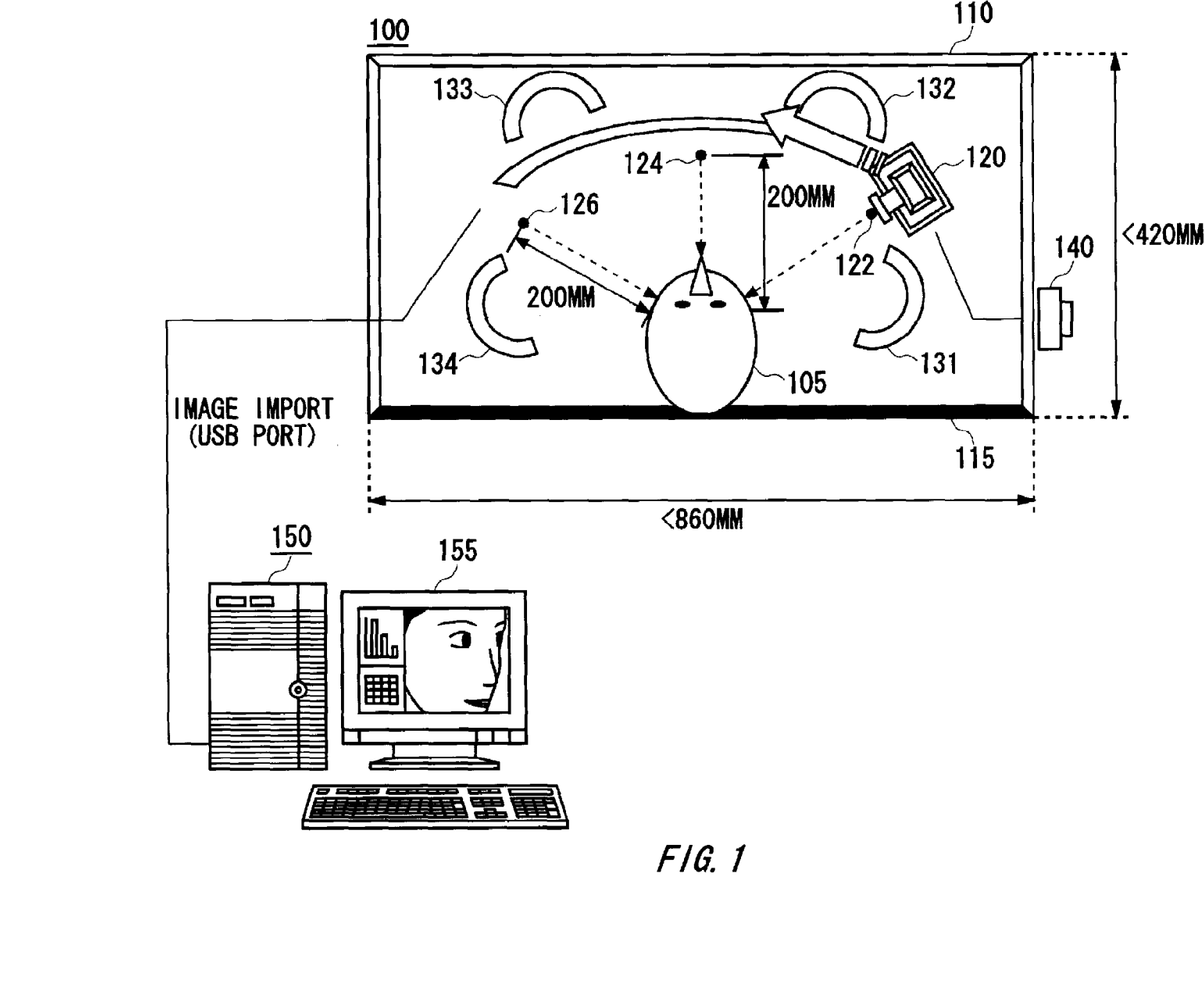
FIG. 1 illustrates an overview of a skin image processing system consistent with the present invention, which includes a skin image capturing box and a computer with a display.

As shown in FIG. 1, a skin image processing system consistent with the present invention includes a skin image capturing box 100 and a computer 150 with a display 155. A client whose face skin is subject to examination puts his/her head 105 into skin image capturing box 100. Walls 110 provide an outer structure for skin image capturing box 100, and among the walls, a back-side one 115 may be formed by a curtain so that the client's head can easily enter inside of box 100.

Inside box 100, a CCD camera 120 is set and controlled to automatically move among a right-45-degree point 122, a front point 124, and a left-45-degree point 126. The points of the movement are not limited to these three, and any number and locations of points may be selected on the arc line whose distance from the surface of the client's face is substantially the same (in this example, 200 mm). In alternative configurations, the right-most and left-most points may be at angles other than 45 degrees (e.g., greater than 45 degrees). CCD camera 120 is positioned at each of the points such that its imaging axis is substantially vertical to the surface of the client's face. As such, the client's face is scanned by the movement of CCD camera 120 for intermittent digital imaging.

CCD camera 120 provides, for example, four million pixels, and takes a high-resolution picture image of the client's face. In this example, three color images are taken per one examination (scan) automatically, i.e., a front face image taken from point 124, a right-side face image taken from point 122, and a left-side face image taken from point 126. To take a picture image manually, a shutter switch 140 is pushed by an operator (e.g., doctor).

The color signals of those images are imported to computer 150 via, for example, USB port. Computer 150 processes those images to produce an analysis result which represents the conditions of face skin. The captured images and/or the computed analysis results are shown to the operator (e.g., doctor), and to the client if desired, via display 155.

Figure 2:
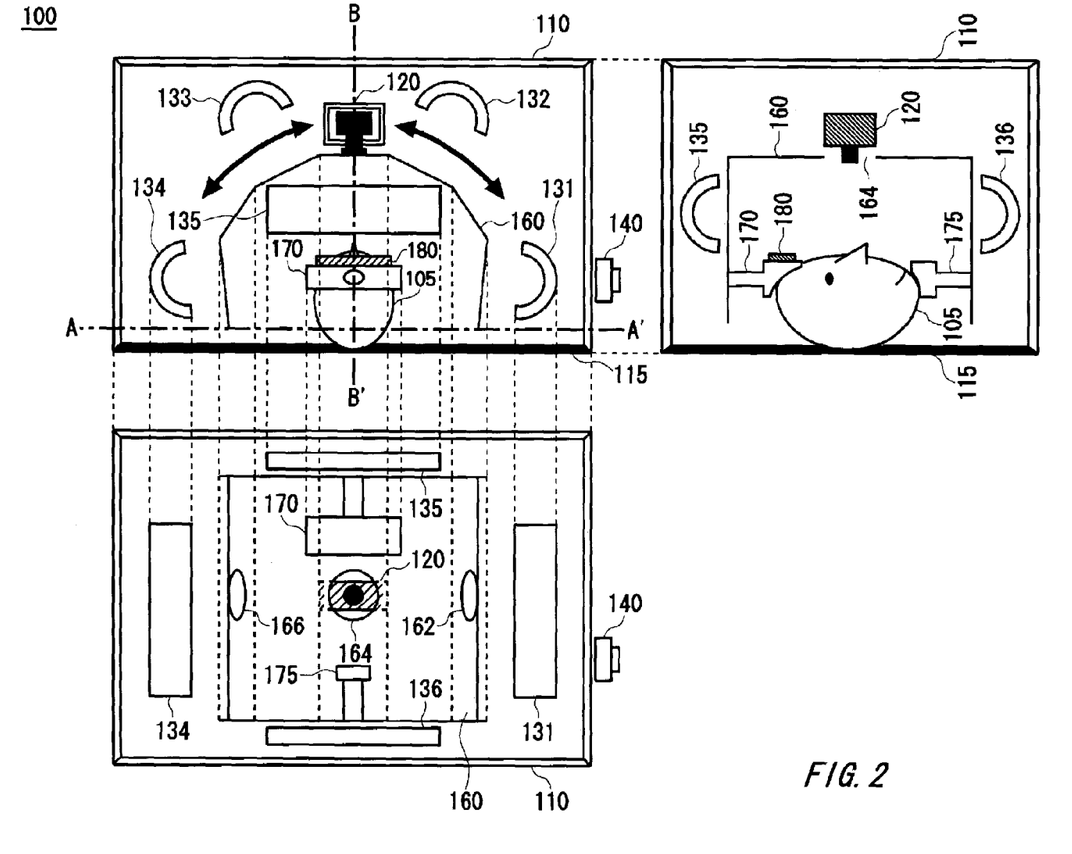
FIG. 2 illustrates an exemplary structure of the skin image capturing box consistent with the present invention, by its perspective view from the top (upper left drawing), lateral view from the face (lower left drawing), and cross-sectional view at the center (upper right drawing)

More details of skin image capturing box 100 are described with reference to FIG. 2. The upper left drawing in FIG. 2 shows a perspective view of box 100 from its top. Four light sources 131 to 134 are placed behind the track of moving camera 120 at substantially equal intervals. Each light source is a standard white light source. Diffused lighting is realized by a diffused board 160 (e.g., milk-white acrylic board) placed between the light sources and the client's face.

The lower left drawing in FIG. 2 shows a cross section along broken line A–A' of box 100 without client's head 105. Diffused board 160 has three holes 162, 164, and 166, which correspond to point 122, 124, and 126, respectively, and enable camera 120 to take a picture image of the client's face. Another light source 135 is placed on the ceiling of box 100, and one more light source 136 is placed on the floor of box 100, both of which are beyond diffused boards from the client's face.

The client's face is fixed by a top-of-head holder 170 and a lower-jaw stand 175. When the client puts his/her jaw on stand 175 and presses his/her upper head into holder 170, the client will see bright milk-white boards in all directions except for three holes for camera 120.

The upper right drawing in FIG. 2 shows a cross section along broken line B–B' of box 100 with client's head 105. On the inner side of top-of-head holder 170, a color chart 180 is placed. Color chart 180 may contain black; white; standard skin color; red; green; and blue. The standard skin color works merely as a basis for comparison, and thus can be determined or created arbitrarily by an operator or manufacturer of box 100. The average of skin colors sampled for each different kind of human race may be used as the standard skin color, and color chart 180 can contain several standard skin colors corresponding to several races.

Illumination sensors (not shown) are placed on both flanks of the client's face in box 100, and the voltages given to light sources 131 to 136 are controlled based on the output of the illumination sensors to keep the illumination in a predetermined range (e.g., 10,000 Lx±3%). In addition, the client's face is fixed by holder 170 and stand 175 at the same position relatively to those of camera 120 and light sources 131 to 136 in each examination, as explained above. Therefore, sufficient repeatability is provided by box 100 for comparing the past and current conditions of one client's skin and/or for comparing one client's conditions with other cases accumulated in a database.

The image of color chart 180 is captured by CCD camera 120 at point 124 as well as the front face image. The output signals from CCD camera 120 corresponding to red, green, blue, and white in color chart 180 are used in correcting color temperature to keep the color sensitivity of CCD in substantially the same condition.

Figure 3:
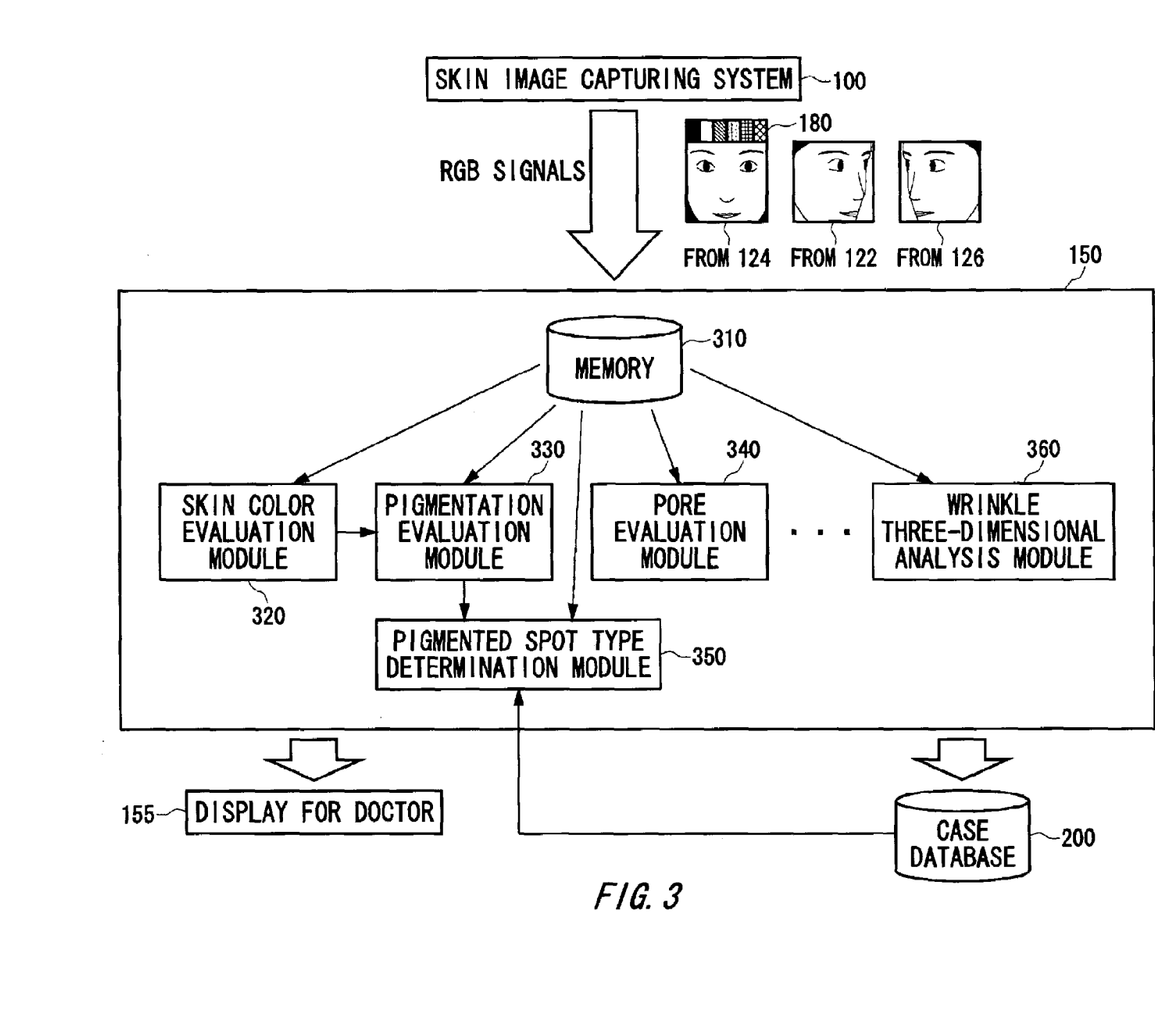
FIG. 3 illustrates an exemplary outline of skin image processing performed by the computer consistent with the present invention.

As shown in FIG. 3, the front face image with the color chart image, the right-side face image, and the left-side face image are imported from skin image capturing box 100 to a memory 310 of computer 150. Each image contains Red (R), Green (G), Blue (B) signals for a large number of pixels.

One or more modules in computer 150 can analyze the skin image stored in memory 310 to produce one or more results representing the skin conditions. These modules can be implemented by software, or by a combination of software and hardware. The results produced by each module can be not only output to display 155 but also stored in case database 200. The RGB signals of the above three face images may be sent to display 155 and case database 200 together with the produced results. This accumulation of the RGB signals along with the evaluation results in case database 200 enables inspection of the past cases referring to the original images. The case name and the individual information such as the client's age, sex, etc. may also be stored along with the evaluation results in case database 200.

A skin color evaluation module 320 in computer 150 processes the skin image stored in memory 310 including RGB signals, and produces "Hue (H), Saturation (S), Value (V)" data, which work as a measure of skin color. These HSV data representing skin color may be output to display 155, and/or accumulated in case database 200. These HSV data may also be used by other evaluation modules to adjust a threshold for distinguishing diseased or damaged (or concerned) portions of the skin, which will be described below, from the client's normal conditioned skin. Here, another color conversion system such as an HSL (Hue, Saturation, Luminosity) color model can substitute for the HSV model.

A pigmentation evaluation module 330 processes the skin image especially of Blue signal to produce "area, number, gray level" data, which indicate a degree of invisible pigmented spots (i.e., a type of damaged portions of the skin). Each invisible pigmented spot is too small to be examined by the naked eye, but module 330 enables this examination focusing on Blue signal of the skin image. The above data regarding invisible pigmented spots may be output to display 155, and/or accumulated in case database 200.

A pore evaluation module 340 processes the skin image especially of Blue signal to produce "area, number, gray level" data, which indicate a degree of conspicuous pores (i.e., another type of damaged portions of the skin). Each conspicuous pore is too small to be examined by the naked eye, but module 340 enables this examination focusing on Blue signal of the skin image. Module 340 can also distinguish the pores from the pigmented spots by their image difference including shape and size. The image difference reflects the fact that the pores are imaged as shadows formed by small round holes on the skin whereas the pigmented spots are arbitrarily shaped melanin cohesion inside the surface of the skin. The above data regarding conspicuous pores may be output to display 155, and/or accumulated in case database 200.

Whereas module 330 is constructed to evaluate merely the invisible pigmented spots, a pigmented spot type determination module 350 processes the skin image to evaluate a more variety of pigmented spots. The pigmented spots in a broad sense include erythema and brown or black pigmented spots in any shape and of any size. The invisible pigmented spots may be considered as a type of pigmented spots, but computer 150 can treat the invisible pigmented spots as another type of damaged portions of the skin than the remainder of the pigmented spots.

The erythema is due to congestion of blood vessels in the dermis of the skin. The brown pigmented spot is due to melanin cohering in the base cell layer under the epidermis of the skin. The black pigmented spot is due to melanin cohering in the epidermis. Due to each wavelength of RGB signals, the Blue signal makes the pigmented spots in the shallow layer, i.e., black ones, appear clearly; the Green signal shows the brown pigmented spots clearly; and the Red signal enables observation of the erythema in the deep layer. Module 350 can acquire three gray levels corresponding to the RGB signals per one pigmented spot in order to examine which cell layer or layers each pigmented spot is formed in.

In this example, module 350 analyzes the Green signal and the Blue signal to find brown and black pigmented spots, respectively. Since the invisible pigmented spots are small ones of the black pigmented spots, a part of the processes performed by module 350 for the Blue signal is the same as those by module 330. Therefore, module 350 can share a part of the processes performed by module 330, and in addition, performs processing of the Green signal. Module 350 further processes the portions extracted as pigmented spots irrespective of their size, and produces "area, shape, gray level in blue and green, distribution" data.

These data produced by module 350 become elements for determining a type of the target pigmented spot. These data regarding the pigmented spot and its determined type may be output to display 155, and/or accumulated in case database 200. The types of the pigmented spots include moth patches, ephelides, and senile pigment freckle, etc.

Case database 200 can store representative "area, shape, gray level, distribution" data for each type of pigmented spot, which may be created automatically by the accumulated data or may be created through manual verification by a doctor. By comparing these representative data with the above data of the target pigmented spot, module 350 can automatically determine the type of the target pigmented spot.

The modules in computer 150 may include a wrinkle three-dimensional analysis module 360, which can calculate three-dimensional shape of a wrinkle from at least two plane images of the face. Module 360 processes Blue signals using the technique of image modeling. Based on the calculated three-dimensional shape, module 360 measures the width, length, and longest depth of the wrinkle. These data of the wrinkles (i.e., yet another type of damaged portions of the skin) may be output to display 155, and/or accumulated in case database 200.

In case of evaluating the wrinkles, CCD camera 120 moves and stops to take picture images at shorter intervals than 45 degrees, and can start the imaging from an arbitrary angle. In this case, diffusing board 160 moves together with CCD camera 120 such that one of holes 162, 164, and 166 of diffusing board 160 is placed on the imaging axis of camera 120. The interval of the intermittent digital imaging during the scan around the client's face by camera 120 may be, for example, 5 degrees, and this angle can be adjusted based on the width, length, and/or location of the wrinkle.

More specifically, the location of the target wrinkle, e.g., on the right-side face or on the left-side face, is first confirmed. CCD camera 120 is then actually moved to the front of the wrinkle, for example, on the left-side face, at the position with an arbitrary angle. Module 360 sets in its software the amount of the movement of camera 120 to, for example, 5 degrees as described above. Thereafter, shutter switch 140 is pushed to start the scan.

Module 360 then inputs one face image taken from the front of the wrinkle, and the other face image taken from the position moved in the direction contrary to the imaged-side (left-side in this example) face by 5 degrees. Module 360 plots the deepest portion of the wrinkle based on the above-input two face images. Module 360 further counts an edge width of the wrinkle and a distance between the deepest portion and the edge in pixels to calculate the longest depth based on the amount of the movement (e.g., tan 5°).

The above evaluation of wrinkles by module 360 using three-dimensional modeling has the following advantages compared to a method of measuring wrinkles using skin images magnified by a microscope. In case of using the video-microscope, the target wrinkle's ditch and mound become deformed by the contact pressure between the skin and the microscope, which results in a significant measurement error. In contrast, wrinkle analysis module 360 consistent with the invention can determine the depth, width, and length of the target wrinkle based on two face images taken from positions isolated from the client's face, and therefore can evaluate the target wrinkle with less errors.

More details of image analysis performed by modules 320, 330, 340, and 350 will described below. Skin color evaluation module 320 performs the skin image analysis according to the flowcharts shown in FIG. 4 (for the front face image) and FIG. 5 (for each of the right-side and left-side face images). Module 320 first identifies flat portions in the face, such as cheek and forehead areas, in order to accurately measure a skin color using the flat portions. An exemplary method for such flat-portion recognition is shown in FIG. 6.

With respect to the front face image, module 320 first inputs the Blue signal (405 in FIG. 4) from memory 310, and performs binarization and edge detection on the Blue image (410). Thereafter, module 320 determines a center of gravity (COG) of each of the right eye area, the left eye area, and the mouth area (420).

Figure 4:
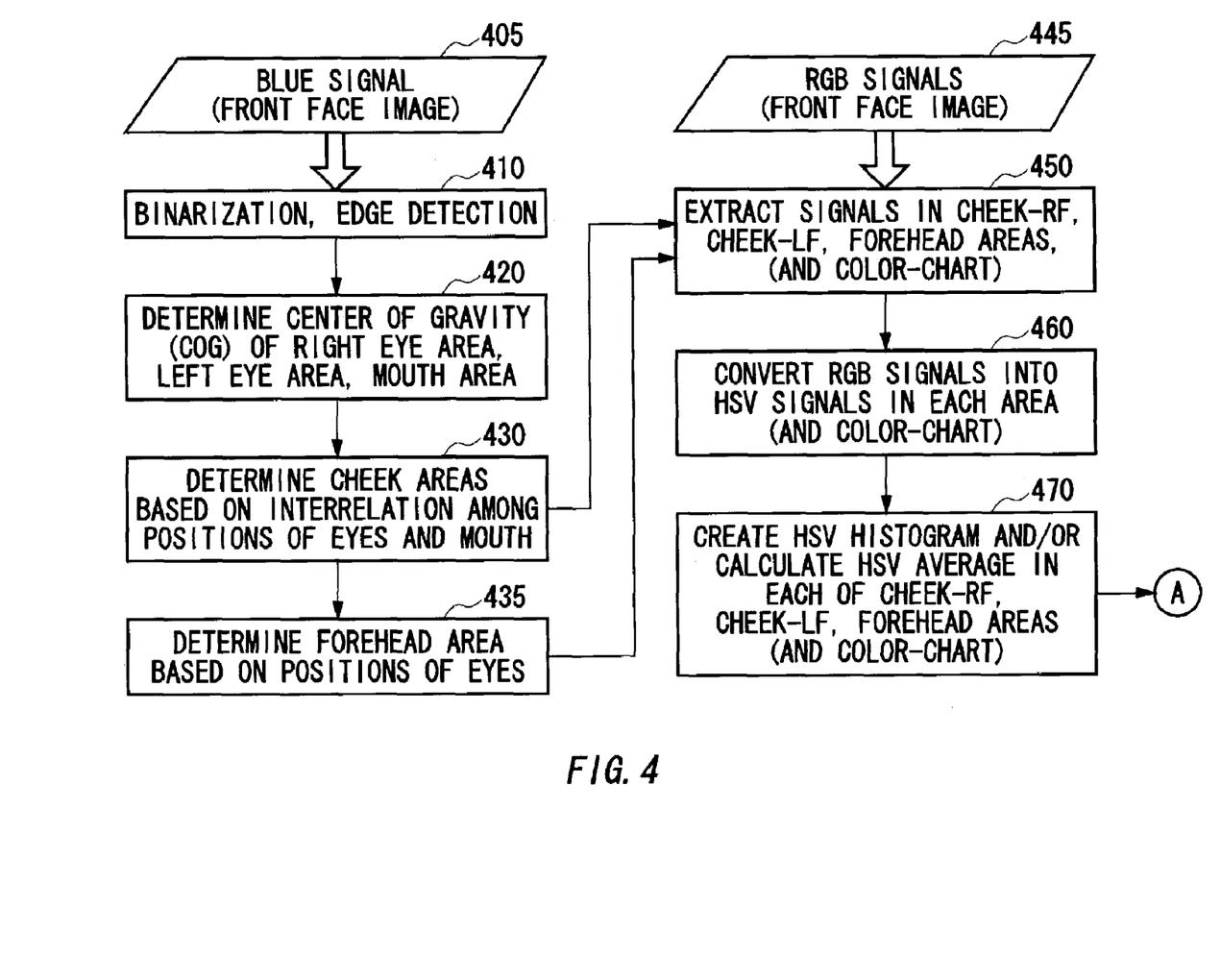
FIG. 4 is a flowchart of an exemplary method of analyzing the skin image for evaluating skin color consistent with the present invention.
Figure 5:
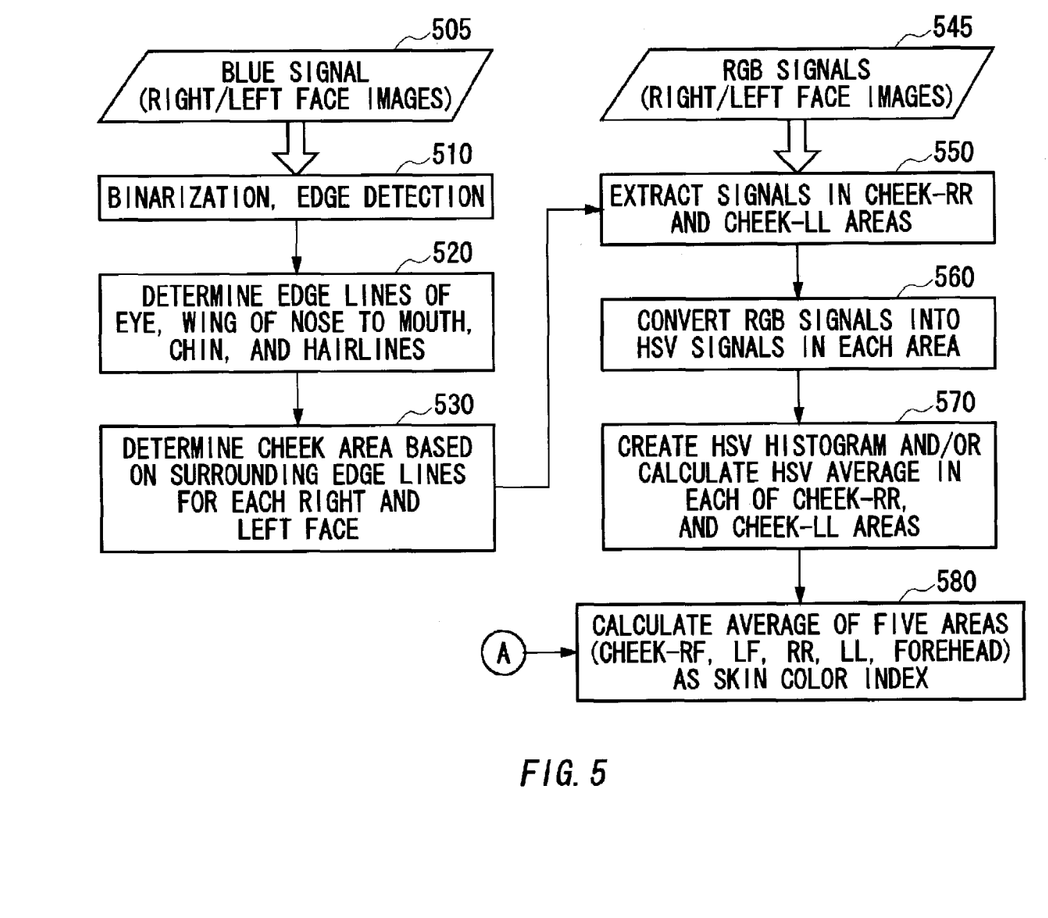
FIG. 5 shows another exemplary method of analyzing the skin image for evaluating skin color consistent with the present invention.

Module 320 then determines a right cheek area in the front face (hereinafter, "cheek-RF" area) and a left cheek area in the front face (hereinafter, "cheek-LF" area) based on the interrelation among the positions of the eyes and mouth represented by their COGs (430). Module 320 also determines a forehead area based on the positions of the eyes (435).

Figure 6A:
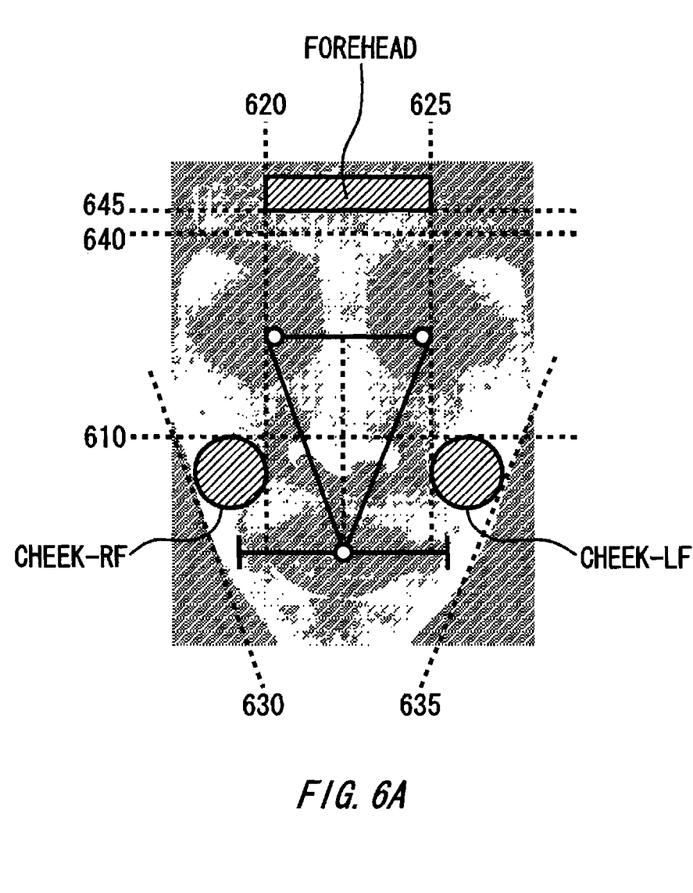
FIG. 6A and FIG. 6B illustrate exemplary operations performed on the front face image and the left-side face image, respectively, in order to determine areas suitable for the skin color evaluation.

More particularly, after the COGs of the eyes and mouth are determined like white circles in FIG. 6A, module 320 draws the first line connecting the right-eye COG and the left-eye COG, and the second line on the mouth COG parallel to the first line. Module 320 then draws line 610 in the middle of the first and second lines at equal distances from both lines. Module 320 further draws perpendicular lines 620 and 625 toward the second (mouth) line from the right-eye and left-eye COGs, respectively, and draws tangent lines 630 and 635 along the right cheek edge and the left cheek edge, respectively. The cheek-RF area is determined as a circular area contacting lines 610, 620, and 630. The cheek-LF area is determined as a circular area contacting lines 610, 625, and 635.

Module 320 further draws horizontal line 640 contacting an upper edge of the eye areas, i.e., eyebrows, and one more horizontal line 645 at one centimeter (cm) above line 640. In this example, one pixel corresponds to approximately 100 micron ($\mu$m) in the actual face, and thus line 645 is apart from line 640 by 100 pixels. The forehead area is determined as a rectangular area surrounding lines 620, 625, and 645 and another horizontal line at six centimeter (cm) above line 640. The height of the rectangular area can be adjusted based on the size of the client's face.

When the three flat areas are determined as above, module 320 extracts the RGB signals (445 in FIG. 4) in these areas from the front face image stored in memory 310 (450). Module 320 may also extracts the RGB signals in the image of color chart 180, especially in the captured image of the standard skin color. Module 320 then converts the extracted RGB signals in each area into HSV signals using, for example, Smith's HSV color models (460). Module 320 may also convert the RGB signals of the color chart's standard skin color into HSV signals for comparison.

Figure 10A:
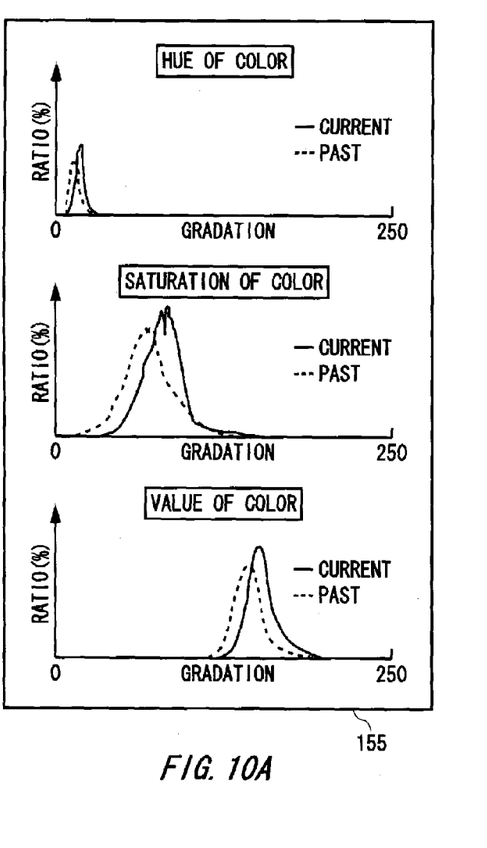
FIG. 10A and FIG. 10B illustrate exemplary information displayed by the computer in case of evaluating the skin color and the pigmented spots, respectively.

Module 320 can create a histogram from each of the HSV signals, as shown in FIG. 10A, by counting the number of pixels having each gradation of Hue, Saturation, and Value (470 in FIG. 4). The HSV histogram may be created for each of the cheek-RF, cheek-LF, and forehead areas, and/or for one combination of all these three areas. In the example of FIG. 10A, each histogram on display 155 shows results of the past and current examinations so that the operator can readily understand the change of the client's skin color. Thus, for example, the operator can confirm the effect of whitening cosmetics.

Alternatively or additionally, module 320 can calculate an average of the HSV signals, such as (H, S, V)=(15, 98, 160) where each gradation varies from 0 to 255 (470 in FIG. 4). This HSV average may be calculated for each of the cheek-RF, cheek-LF, and forehead areas, and may be calculated also for the standard skin color of color chart 180 to determine the difference of the client's skin color in each area from the standard skin color.

With respect to the side face image, module 320 first inputs the Blue signal (505 in FIG. 5) from memory 310, and performs binarization and edge detection on the Blue image (510). Thereafter, module 320 determines edge lines surrounding the cheek area (520). Using these edge lines, a right cheek area in the right-side face (hereinafter, "cheek-RR" area) and a left cheek area in the left-side face (hereinafter, "cheek-LL" area) are determined on the right-side face image and the left-side face image, respectively (530).

Figure 6B:
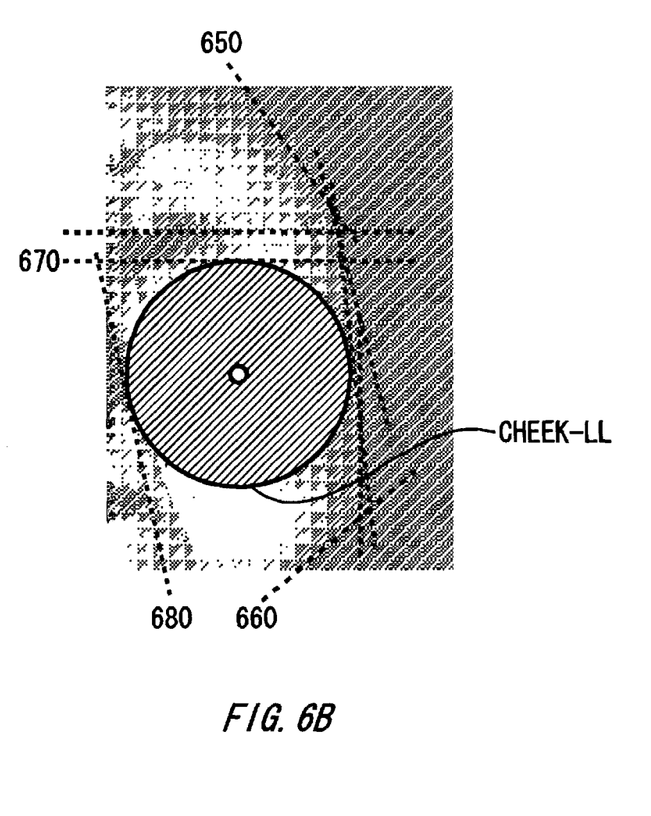

More particularly, as shown in FIG. 6B (the left-side face example), module 320 draws edge lines 650 corresponding to the hairlines, and tangent line 660 along the chin line. Module 320 further draws horizontal line 670 contacting a lower edge of the eye, and line 680 along one (the left-side one in this example) of the wings of the nose extending to one end (the left-side end in this example) of the mouth. A COG of the portion surrounded by edge lines 650, 660, 670, and 680 is then determined. The cheek-LL area is determined as a circular area whose center is the COG of the surrounded portion and whose radius is selected to be the maximum contacting some of the edge lines. The cheek-RR area is determined similarly on the right-side face image (not shown).

When the flat area for each side face image is determined as above, module 320 extracts the RGB signals (545 in FIG. 5) in this area from the corresponding side face image stored in memory 310 (550). Module 320 then converts the extracted RGB signals in each area into HSV signals using, for example, Smith's HSV color models (560).

Module 320 can create a histogram from each of the HSV signals, for each of the cheek-RR and cheek-LL areas, and/or for one combination of these two areas (570). Further, module 320 can input the HSV data of the other three areas acquired according to the flowchart of FIG. 4, and create the HSV histogram for one combination of all the five (cheek-RF, LF, RR, LL, and forehead) areas (580 in FIG. 5).

Alternatively or additionally, module 320 can calculate an average of the HSV signals for each of the cheek-RR and cheek-LL areas (570). As a result of the analysis shown in FIG. 4 and FIG. 5, the HSV average, such as (H, S, V)=(15, 98, 160), is produced for each of the five (cheek-RF, LF, RR, LL, and forehead) areas, as the client's skin color indices. The skin color indices may be expressed as the difference of the client's skin color (HSV average) in each area from the standard skin color (HSV average) in the color chart.

For further data compression, only one HSV average can represent the client's skin color. An exemplary compression is an average of the HSV indices of the five areas.

Figure 7:
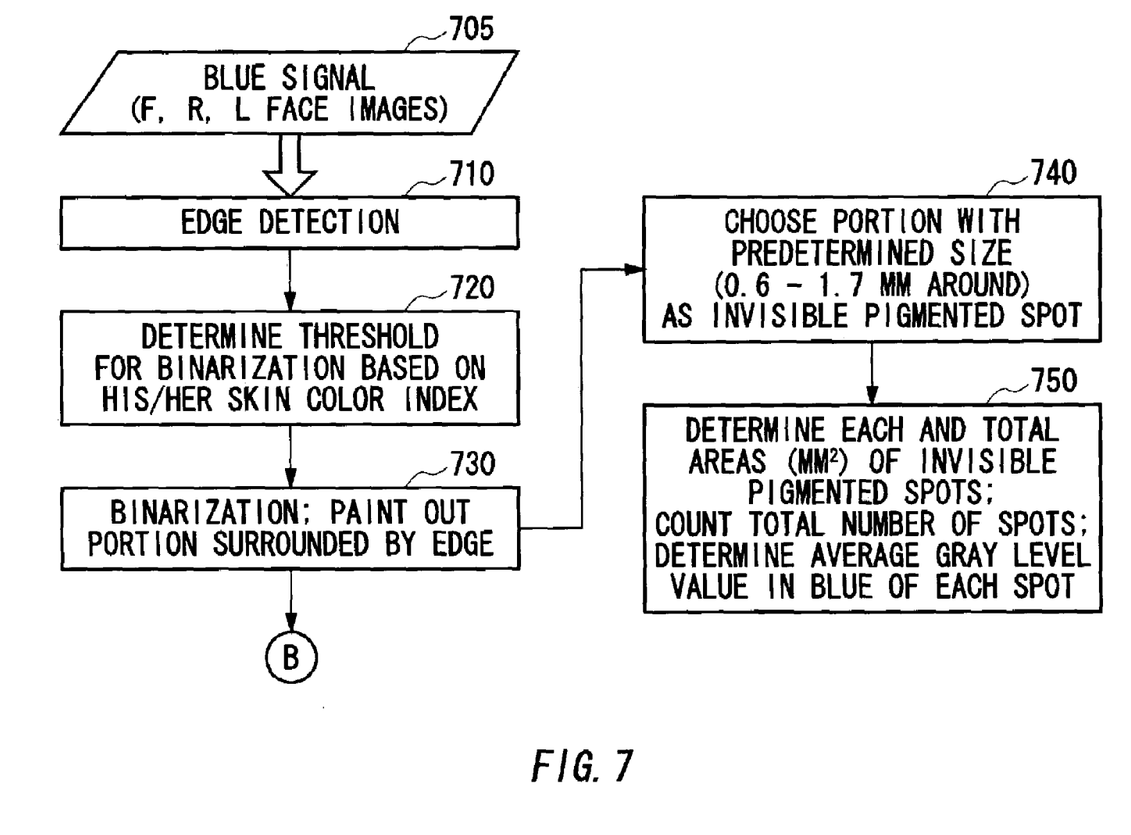
FIG. 7 is a flowchart of an exemplary method of analyzing skin image for evaluating invisible pigmented spots consistent with the present invention.

Pigmentation evaluation module 330 performs the skin image analysis according to the flowcharts shown in FIG. 7. The operations indicated in FIG. 7 are done on the front, right-side, and left-side face images separately.

Module 330 inputs the Blue signal (705) from memory 310, and performs smoothing on the Blue image for noise removal. Module 330 then performs edge detection (710), because pigmented spots often have unclear boundaries.

Module 330 performs binarization on the Blue image (730), and before that, determines a threshold for the binarization based on the client's skin color indices (720). The skin color indices determined by module 320 as described above can identify a possible range of the client's skin color, and the threshold for the binarization is determined to be a lower (darker) level than the identified possible range of the skin color. For example, the threshold for identifying pigmented spots is selected in the range of 80–130 where the gray level varies from 0 to 255. After binarization, module 330 paints out each portion surrounded by the detected edge (730).

Since module 330 concentrates its objective on the invisible pigmented spots, it chooses among the painted portions the ones whose size is within a predetermined range, e.g., 0.6–1.7 mm (740). Thereafter, module 330 counts the number of black pixels surrounded by the edge and painted out in each portion chosen as an invisible pigmented spot to determine its area (in units of pixels or converted into mm$^2$) (750). Module 330 also calculates the sum of the areas of all portions chosen as invisible pigmented spots, and counts the total number of the invisible pigmented spots (750). Module 330 further calculates an average gray level in the Blue signal (705) of each invisible pigmented spot (750).

These "area, number, gray level" data separately acquired from the three (front, right-side, left-side) face images are all accumulated in case database 200. As to the double or triple counted pigmented spots via the three images, their data may be stored as they are. The client's currently acquired data can be statistically compared on the spot with many data in case database 200 that categorized in the same age, sex, etc. as the client, in order to determine a degree of the invisible pigmented spots of the client.

Figure 8:
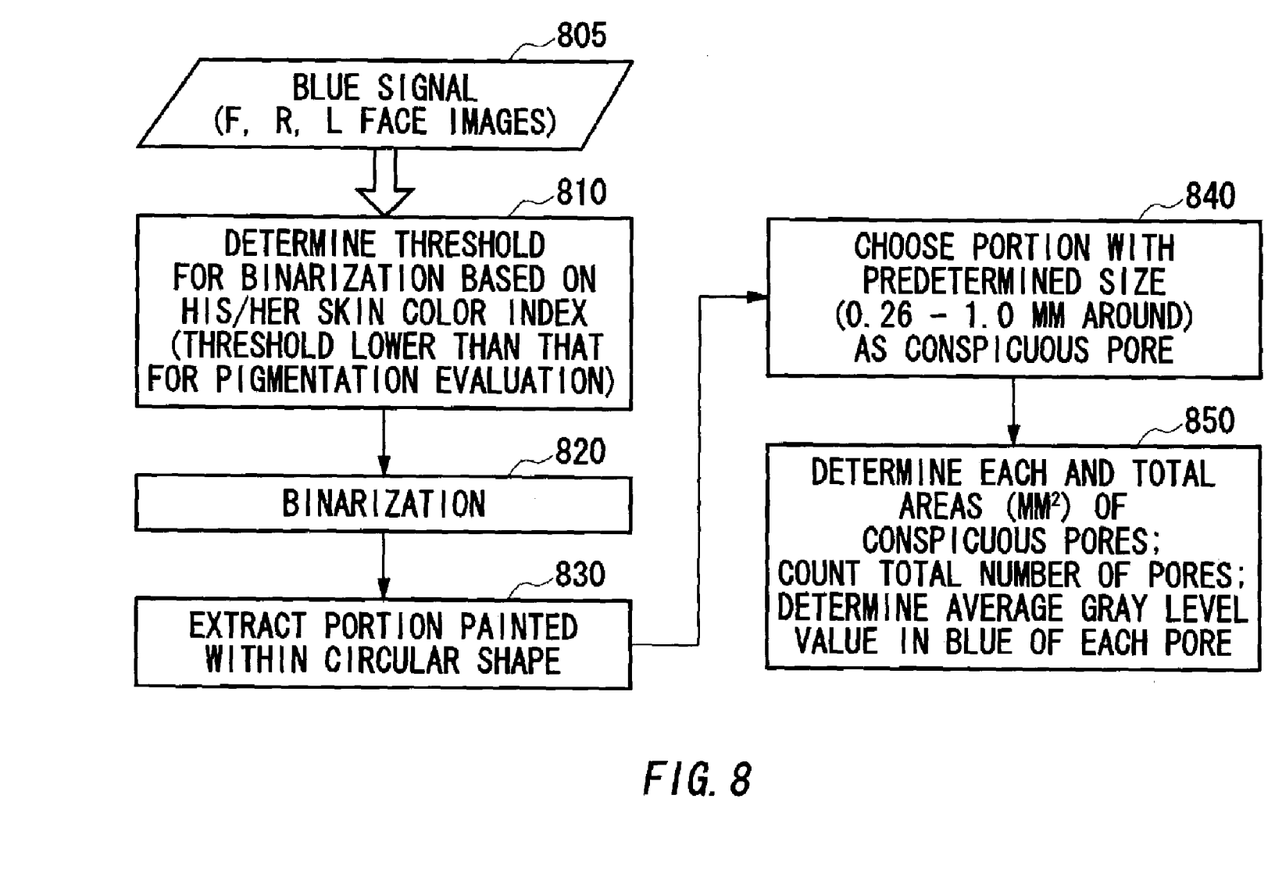
FIG. 8 is a flowchart of an exemplary method of analyzing skin image for evaluating conspicuous pores consistent with the present invention.

Pore evaluation module 340 performs the skin image analysis according to the flowcharts shown in FIG. 8. The operations indicated in FIG. 8 are done on the front, right-side, and left-side face images separately.

Module 340 inputs the Blue signal (805) from memory 310, and performs smoothing on the Blue image for noise removal. Module 340 performs neither edge detection nor painting out any portion surrounded by the edge, because boundaries of pores are generally clear in the captured image and smaller than the invisible pigmented spots.

Module 340 performs binarization on the Blue image (820), and before that, determines a threshold for the binarization based on the client's skin color indices (810). The skin color indices determined by module 320 as described above can identify a possible range of the client's skin color, and the threshold for the binarization is determined to be a much lower (darker) level than the identified possible range of the skin color. The threshold of binarization for pores is determined to be lower (darker) than that for pigmented spots. For example, the threshold for identifying pores is selected in the range of 0–80 where the gray level varies from 0 to 255.

After binarization, module 340 identifies a portion formed by black pixels gathering in a circular shape (830), and chooses among the identified portions the ones whose size is within a predetermined range, e.g., 0.26–1.0 mm as conspicuous pores (840). Thereafter, module 340 counts the number of black pixels in each portion chosen as a conspicuous pore to determine its area (in units of pixels or converted into $mm^2$) (850). Module 340 also calculates the sum of the areas of all portions chosen as conspicuous pores, and counts the total number of the conspicuous pores (850). Module 340 further calculates an average gray level in the Blue signal (805) of each conspicuous pore (850).

These "area, number, gray level" data separately acquired from the three (front, right-side, left-side) face images are all accumulated in case database 200. As to the double or triple counted pores via the three images, their data may be stored as they are. The client's currently acquired data can be statistically compared on the spot with many data in case database 200 that categorized in the same age, sex, etc. as the client, in order to determine a degree of aggravation of pores of the client.

Figure 9:
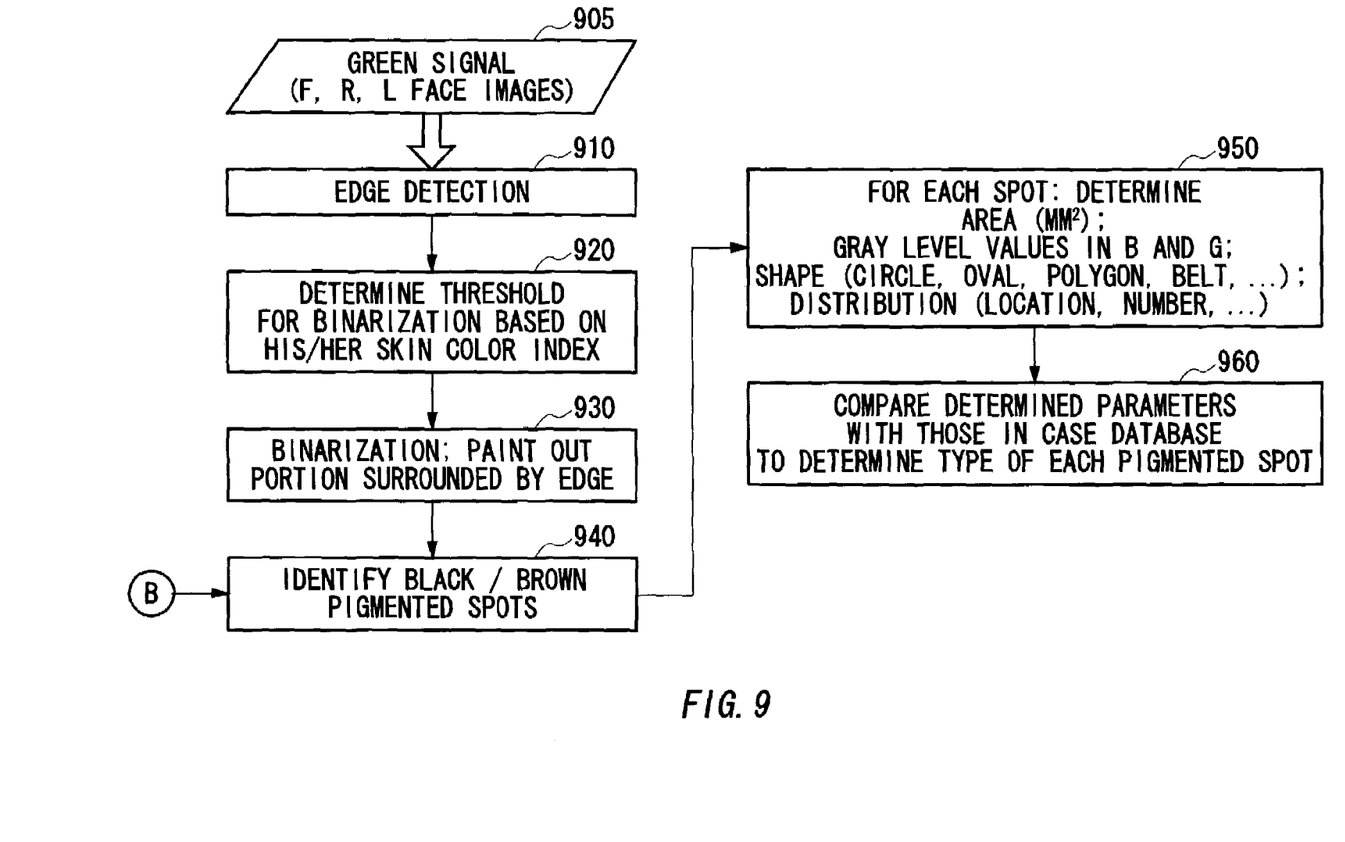
FIG. 9 is a flowchart of an exemplary method of analyzing skin image for determining types of pigmented spots consistent with the present invention.

Pigmented spot type determination module 350 performs the skin image analysis according to the flowcharts shown in FIG. 9. The operations indicated in FIG. 9 are done on the front, right-side, and left-side face images separately.

Module 350 inputs the Green signal (905) from memory 310, and performs smoothing on the Green image for noise removal. Module 350 then performs edge detection (910), because pigmented spots often have unclear boundaries.

Module 350 performs binarization on the Green image (930), and before that, determines a threshold for the binarization based on the client's skin color indices (920). The skin color indices determined by module 320 as described above can identify a possible range of the client's skin color, and the threshold for the binarization is determined to be a lower (darker) level than the identified possible range of the skin color. After binarization, module 350 paints out each portion surrounded by the detected edge (930).

The above processing (910 to 930) on the Green image is similar to that (710 to 730) on the Blue image shown in FIG. 7, and module 350 thereafter can identify all black and brown pigmented spots on the Blue and Green images, respectively (940). Module 350 counts the number of dark pixels surrounded by the edge and painted out in each portion chosen as a black or brown pigmented spot to determine its area (in units of pixels or converted into $mm^2$) (950). Module 350 also determines which type of shape (e.g., circle, oval, polygon, belt, etc.) each pigmented spot has, and may classify the state of the edge of each pigmented spot also (950).

Module 350 further calculates an average gray level in each of the Blue and Green signals (705, 905) of each black or brown pigmented spot (950). Module 350 further determines distribution of the pigmented spots, e.g., how many pigmented spots exist in what location of the face (950).

Thereafter, module 350 compares these "area, shape, gray level, distribution" parameters with those stored in case database 200 (960). As a result, the type of pigmented spot whose data are statistically similar to those of the currently examined client is determined to be the type of the target pigmented spot of the client.

Figure 10B:
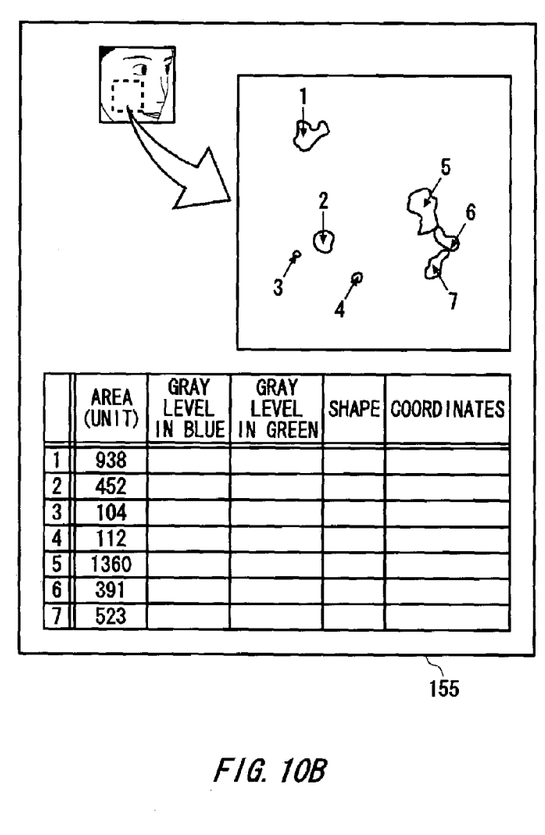

The analysis results of module 350 may be displayed as shown in FIG. 10B. In this example, display 155 shows a captured RGB face image, and a processed Blue or Green image after edge detection, binarization, and painting out, in which seven pigmented spots 1, 2, 3, 4, 5, 6, 7 are identified. Display 155 also shows a table containing the "area, shape, gray level, distribution" data for each of the seven pigmented spots. The analysis results of module 330 or 340 can be displayed similarly to FIG. 10B.

As explained in detail above, methods and systems consistent with the invention enable evaluation of the skin conditions based on more than one areas in the entire face at once. The face image including more than one areas can be captured via merely one shot of a digital camera. Furthermore, a desirable number of images of the entire face can be taken via scanning the surface of the face from the positions isolated by a substantially equal distance, with intermittent digital imaging by the moving camera.

Such methods and systems have an advantage, compared to the use of a video-microscope, in that they can determine parameters representing the skin conditions not only for one concerned portion but also for the entire face. The parameters for the entire face include the total number of invisible pigment spots or conspicuous spots, the distribution of a particular type of pigmented spots, or the like. In addition, such methods and systems facilitate evaluation of the effects of a clinical testing on a client in which two or more medicines different in efficacy are separately applied to different areas, e.g., on the right side and on the left side of the face.

Moreover, compared to the use of a colorimeter for skin color and another diagnosis method for pigmented spots, methods and systems consistent with the invention can analyze the captured skin images for more general purposes. That is, methods and systems consistent with the invention can evaluate the skin conditions from two or more aspects, i.e., measure two or more types of damaged portions of the skin at once based on merely one image.

Persons of ordinary skill in the art will realize that many modifications and variations of the above embodiments may be made without departing from the novel and advantageous features of the present invention. For example, the examination target of the above embodiments is the skin of human face, but methods and systems consistent with the invention can inspect the integument of other portions of human body, such as the back, the chest, a joint, or the like. Further, yet another type of damaged portions like skin lesions can be digitally evaluated based on the skin images captured by the above-explained system.

Accordingly, all such modifications and variations are intended to be included within the scope of the appended claims. The specification and examples are only exemplary. The following claims define the true scope and spirit of the invention.

What is claimed is:

1. A skin image processing system comprising:
an image capturing device for moving a camera to acquire a plurality of digital images for one human body, each of the digital images representing a surface of a portion of the human body, the surface being illuminated with white light and placed apart from the camera;
a receiving unit configured to receive the digital images from the camera;
a processing unit configured to perform a plurality of kinds of analysis on the digital images received by the receiving unit to produce a plurality of data representing skin conditions of the human body; and
an output unit configured to output the plurality of data produced by the processing unit.

2. The system according to claim 1, wherein the processing unit processes color signals included in at least one of the digital images to evaluate a skin color of the portion of the human body, as one of the plurality of kinds of analysis.

3. The system according to claim 2, wherein the processing unit processes at least one of the color signals to determine at least one flat area in the portion of the human body, and uses the color signals of said at least one flat area in said at least one of the digital images for evaluation of the skin color.

4. The system according to claim 2, wherein the processing unit performs another one of the plurality of kinds of analysis on said at least one of the digital images, using a result of evaluation of the skin color.

5. The system according to claim 1, wherein the processing unit processes a color signal with a predetermined wavelength among color signals included in at least one of the digital images to evaluate pigmented spots formed in a shallow layer of skin of the portion of the human body, as one of the plurality of kinds of analysis.

6. The system according to claim 5, wherein the processing unit processes the color signal to detect edge lines of dark sections on said at least one of the digital images and to choose sections surrounded by the edge lines, the section's size being in a predetermined range, for evaluation of a degree of invisible pigmented spots.

7. The system according to claim 1, wherein the processing unit processes a color signal with a predetermined wavelength among color signals included in at least one of the digital images to evaluate pores existing on the surface of skin of the portion of the human body, as one of the plurality of kinds of analysis.

8. The system according to claim 7, wherein the processing unit processes the color signal to choose dark sections formed in a circular shape on said at least one of the digital images, the dark section's size being in a predetermined range, for evaluation of a degree of conspicuous pores.

9. The system according to claim 1, wherein the processing unit processes at least two color signals among color signals included in at least one of the digital images to evaluate pigmented spots formed in various layers of skin of the portion of the human body, as one of the plurality of kinds of analysis.

10. The system according to claim 1, wherein the processing unit processes at least one color signal among color signals included in at least one of the digital images to determine a type of a pigmented spot formed in skin of the portion of the human body, as one of the plurality of kinds of analysis, by comparing parameters computed regarding the pigmented spot with parameters stored in a database as known cases.

11. The system according to claim 1, wherein the processing unit processes at least one color signal among color signals included in two or more of the digital images to evaluate a wrinkle existing on the surface of skin of the portion of the human body through three-dimensional modeling, as one of the plurality of kinds of analysis.

12. The system according to claim 1, wherein the output unit stores the plurality of data representing skin conditions of the portion of the human body into a database, and
the processing unit refers to the plurality of data stored in the database to perform at least one of the plurality of kinds of analysis on another set of digital images received by the receiving unit.

13. The system according to claim 1, wherein the portion of the human body is one of a front face, a right-side face, and a left-side face.

14. The system according to claim 1 wherein the image capturing device further includes:
a tool for providing the portion of the human body with a fixed place to be disposed; and
the white light for providing the fixed place with indirect lighting.

15. The system according to claim 14, wherein the image capturing device moves the camera, keeping a predetermined distance from the fixed place.

16. The system according to claim 1, wherein the receiving unit receives the digital images in which a plurality of areas on the surface of the human body are to be determined, and
the processing unit produces data representing skin conditions for each of the plurality of areas on the surface of the human body.

17. A method of skin image analysis by a computer comprising:
moving a camera to acquire a plurality of digital images for one human body, each of the digital images representing a surface of a portion of the human body, the surface being illuminated with white light and placed apart from the camera;
receiving the digital images from the camera;
performing a plurality of kinds of analysis on the digital images to produce a plurality of data representing skin conditions of the human body; and
displaying at least one of the digital images and the data representing the skin conditions.

18. The method of claim 17, wherein the camera is moved, making a distance from the camera to the portion of the human body within a predetermined range.

19. The method of claim 18, wherein at least one of the plurality of kinds of analysis is performed on the plurality of digital images acquired by moving the camera to produce data representing skin conditions for each of the plurality of digital images, the digital images including a plurality of areas on the surface of the human body.

20. A computer usable medium having computer readable program code units embodied therein for a computer functioning as a skin image processing system, the computer readable program code units causing the computer to perform a method comprising:
  connecting the computer to a camera, the camera being moved to acquire a plurality of digital images for one human body, each of the digital images representing a surface of a portion of the human body, the surface being illuminated with white light and placed apart from the camera;

receiving the digital images from the camera;

performing a plurality of kinds of analysis on the digital images to produce a plurality of data representing skin conditions of the human body; and outputting the plurality of data representing skin conditions of the human body.

* * * * *